United States Patent
Govari

(10) Patent No.: US 11,185,274 B2
(45) Date of Patent: Nov. 30, 2021

(54) IDENTIFYING ORTHOGONAL SETS OF ACTIVE CURRENT LOCATION (ACL) PATCHES

(71) Applicant: Biosense Webster (Israel) Ltd., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 103 days.

(21) Appl. No.: 16/010,573

(22) Filed: Jun. 18, 2018

(65) Prior Publication Data
US 2019/0380608 A1    Dec. 19, 2019

(51) Int. Cl.
| A61B 5/316 | (2021.01) |
| A61B 5/0538 | (2021.01) |
| A61B 5/282 | (2021.01) |
| A61B 5/287 | (2021.01) |

(52) U.S. Cl.
CPC ............ *A61B 5/316* (2021.01); *A61B 5/0538* (2013.01); *A61B 5/282* (2021.01); *A61B 5/287* (2021.01)

(58) Field of Classification Search
USPC .................................................. 600/509, 512
See application file for complete search history.

(56) References Cited

U.S. PATENT DOCUMENTS

| 5,697,377 | A | 12/1997 | Wittkampf |
| 5,899,860 | A | 5/1999 | Pfeiffer et al. |
| 5,983,126 | A | 11/1999 | Wittkampf |
| 7,756,576 | B2 | 7/2010 | Levin |
| 7,848,787 | B2 | 12/2010 | Dsadchy |
| 7,869,865 | B2 | 1/2011 | Altmann et al. |
| 8,456,182 | B2* | 6/2013 | Bar-Tai .................. A61B 5/053 324/713 |
| 8,611,991 | B2 | 12/2013 | McEwan et al. |
| 9,615,764 | B2* | 4/2017 | Zino ...................... A61B 5/062 |
| 2007/0038078 | A1 | 2/2007 | Dsadchy |
| 2007/0060833 | A1 | 3/2007 | Hauck |

(Continued)

FOREIGN PATENT DOCUMENTS

WO    2008108901 A1    9/2008

OTHER PUBLICATIONS

Extended European search report for corresponding European patent application No. EP 19180644.7, dated Nov. 26, 2019.

*Primary Examiner* — Gary Jackson
*Assistant Examiner* — Anant A Gupta
(74) *Attorney, Agent, or Firm* — Notaro, Michalos & Zaccaria P.C.

(57) ABSTRACT

A position tracking system includes an electrical interface and a processor. The electrical interface is configured to communicate with one or more electrodes that are coupled to a distal end of a probe inserted into a heart of a patient. The electrical interface is further configured to receive, from a plurality of electrode-patches attached to a skin of the patient, position signals that are indicative of positions of the one or more electrodes in the heart. The processor is configured to select, based on the position signals, a partial subset of the electrode-patches whose position signals are least-correlated with one another, and to estimate a position of at least one of the electrodes in the heart, based on the position signals received from the selected partial subset of the electrode-patches.

10 Claims, 3 Drawing Sheets

(56) References Cited

U.S. PATENT DOCUMENTS

| | | |
|---|---|---|
| 2012/0226110 A1 | 9/2012 | Markowitz et al. |
| 2013/0066193 A1 | 3/2013 | Olson et al. |
| 2016/0235339 A1 | 8/2016 | Bar-Tal et al. |
| 2017/0079542 A1 | 3/2017 | Spector |
| 2017/0105680 A1* | 4/2017 | Shushan .............. A61B 5/6869 |

* cited by examiner

IDENTIFYING ORTHOGONAL SETS OF ACTIVE CURRENT LOCATION (ACL) PATCHES

FIELD OF THE INVENTION

The present invention relates generally to systems and methods for tracking catheter position within a patient's heart, and specifically to impedance based cardiac position tracking systems and methods.

BACKGROUND OF THE INVENTION

Tracking the position of an intrabody mapping catheter is required in many cardiac procedures. For example, U.S. Patent Application Publication 2017/0079542 describes a method for identifying an electrode tissue contact quality comprising positioning a catheter including an array of at least a first electrode and a second electrode affixed to the catheter and having a known inter-electrode spacing in the vicinity of a cardiac tissue, wherein each electrode pair is configured to be orthogonal to a surface of a cardiac tissue substrate. The method comprises measuring a first rate of change in electrogram amplitude from the first electrode, measuring a second rate of change in electrogram amplitude from the second electrode, calculating a difference between the first rate of change in electrogram amplitude and the second rate of change in electrogram amplitude to obtain a difference between rate of changes, and correlating the difference in rate of changes value to whether the first electrode is in contact with the cardiac tissue.

As another example, U.S. Pat. No. 5,983,126 describes a system and method for catheter location mapping, and related procedures. Three substantially orthogonal alternating signals are applied through the patient, directed substantially toward the area of interest to be mapped, such as patient's heart. A catheter is equipped with at least a measuring electrode, which for cardiac procedures is positioned at various locations either against the patient's heart wall, or within a coronary vein or artery. A voltage is sensed between the catheter tip and a reference electrode, preferably a surface electrode on the patient, which voltage signal has components corresponding to the three orthogonally applied current signals. Three processing channels are used to separate out the three components as x, y and z signals, from which calculations are made for determination of the three-dimensional location of the catheter tip within the body.

U.S. Pat. No. 8,611,991 describes a method for taking electrical impedance tomography measurements using multiple electrodes located at selected positions external to a volume of a subject body. Multiple orthogonal or near-orthogonal signals are introduced simultaneously by way of selected different electrodes and resultant predetermined responses (if any) at receiving electrodes are recorded or determined. The signals are encoded using the technique of code division multiplexing and received signals at each receiving electrode are cross-correlated with original signals to determine the contribution of each original signal to a composite received signal.

U.S. Pat. No. 5,899,860 describes a system for determining the position of a catheter inside the body of a patient. A correction function is determined from the difference between calibration positions derived from received location signals and known, true calibration positions, whereupon catheter positions, derived from received position signals, are corrected in subsequent measurement stages according to the correction function.

U.S. Pat. No. 5,697,377 describes techniques for catheter location mapping. Three substantially orthogonal alternating signals are applied through the patient, directed substantially toward the area of interest to be mapped. A catheter is equipped with at least a measuring electrode. A voltage is sensed between the catheter tip and a reference electrode, preferably a surface electrode on the patient, which voltage signal has components corresponding to the three orthogonal applied current signals. Three processing channels are used to separate out the three components as x, y and z signals, from which calculations are made for determination of the three-dimensional location of the catheter tip within the body.

SUMMARY OF THE INVENTION

An embodiment of the present invention that is described herein provides a position tracking system including an electrical interface and a processor. The electrical interface is configured to communicate with one or more electrodes that are coupled to a distal end of a probe inserted into a heart of a patient. The electrical interface is further configured to receive, from a plurality of electrode-patches attached to a skin of the patient, position signals that are indicative of positions of the one or more electrodes in the heart. The processor is configured to select, based on the position signals, a partial subset of the electrode-patches whose position signals are least-correlated with one another, and to estimate a position of at least one of the electrodes in the heart, based on the position signals received from the selected partial subset of the electrode-patches.

In some embodiments, the processor is configured to select the least-correlated electrode-patches by sequentially selecting one electrode-patch from each possible pair of the electrode-patches, such that the one electrode-patch of the pair measures a smallest change in position signal as the other electrode-patch measures a changing position signal while the distal end moves in the heart.

In some embodiments, the processor is configured to select different subsets of least-correlated position signals for different regions in the heart.

In an embodiment, the processor is configured to provide three least-correlated position signals as elements of a 3×3 matrix.

In another embodiment, the electrical interface is further configured to receive the position signals from the one or more electrodes that are coupled to the distal end of the probe.

There is additionally provided, in accordance with an embodiment of the present invention, a position tracking method, the method including communicating with one or more electrodes that are coupled to a distal end of a probe inserted into a heart of a patient. Position signals that are indicative of positions of the one or more electrodes in the heart are received from a plurality of electrode-patches attached to a skin of the patient. Based on the position signals, a partial subset of the electrode-patches whose position signals are least-correlated with one another is selected. Based on the position signals received from the selected partial subset of the electrode-patches, a position of at least one of the electrodes in the heart is estimated.

The present invention will be more fully understood from the following detailed description of the embodiments thereof, taken together with the drawings in which:

DETAILED DESCRIPTION OF EMBODIMENTS

Overview

Figure 1:
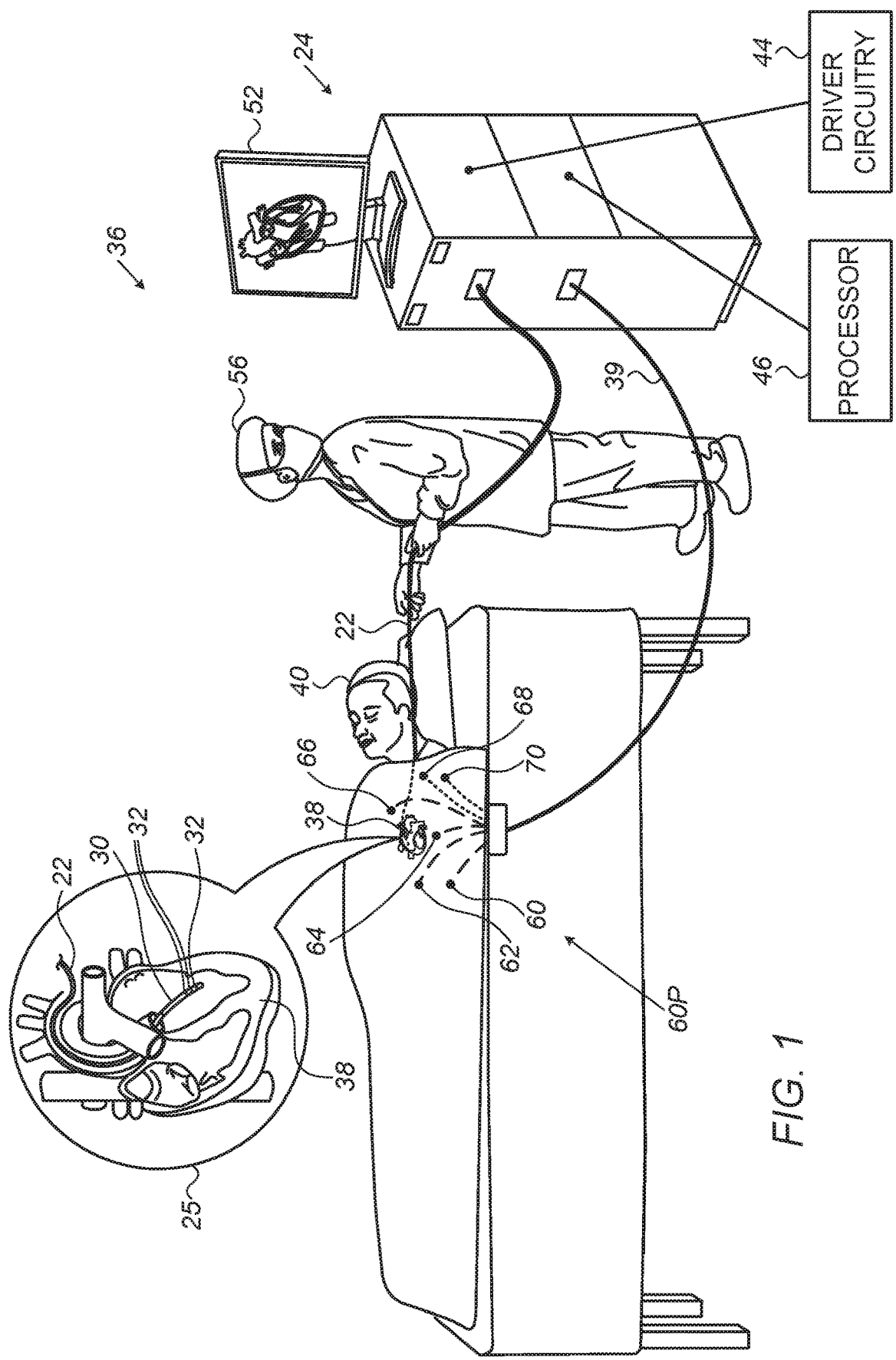
FIG. 1 is a schematic, pictorial illustration of an impedance based Active Current Location (ACL) position tracking system, in accordance with an embodiment of the present invention.

Several approaches may be used for tracking a position inside a body of a patient. Impedance-based position tracking methods, for example, may either assume that measured impedances between one or more intra-body sensing-electrodes and surface-electrodes are proportional to respective distances, or calibrate measured impedances by correlating the impedances with respective coordinates measured in advance. Voltage-based sensing methods, on the other hand, use the one or more intra-body sensing-electrodes for sensing surface-electrodes.

Impedance-based position tracking systems typically measure impedances between a sensing-electrode and the surface-electrodes (named hereinafter 'electrode-patches') attached to the skin, and from these measurements derive a three-dimensional position coordinate of the sensing-electrode. In principle, three electrode-patches are sufficient for triangulating the position of a sensing-electrode, using well known methods described, for example, in U.S. Pat. No. 7,756,576, whose disclosure is incorporated herein by reference.

Voltage-based position tracking systems typically measure voltages between a sensing-electrode and the electrode-patches (i.e., the sensing-electrodes are used for measuring voltages induced between ACL patches). In this case, four electrode-patches are sufficient for triangulating the position of a sensing-electrode, so as to generate three different voltage gradients that the sensing-electrodes measures.

In practice, either three-electrode-patches schemes with impedance-based methods, or four-electrode-patches schemes with voltage-based methods, achieve insufficient position accuracy. Thus, to accurately measure an intra-body position of a sensing-electrode, impedance-based position tracking systems, such as the Active Current Location (ACL) system (produced by Biosense Webster, Inc.), use a larger number of patches. Voltage-based position tracking systems, such as the CARTO4® (produced by Biosense Webster, Inc.) also use larger number of patches. An ACL system, for example, either impedance based or voltage based, may use six or more patches, named hereinafter 'ACL patches.' The ACL patches are attached to the patient skin on the chest and the back, an arrangement found to consistently and reliably triangulate any given three-dimensional position in a heart. The position of the sensing-electrodes is given in a coordinate system defined by the six ACL patches and an arbitrary origin within the three-dimensional space.

Deriving in real-time accurate electrode-positions from impedance-based measurements puts demanding computational requirements on multiple-patch tracking position systems. Unless expansive computing hardware is employed, the complicated calculations involved may cause disturbing delays, for example between necessary updates of a position map that is presented to the physician on a display. Such delays may result in inaccuracies in maps, especially with maps of a moving organ like a chamber of a heart.

Embodiments of the present invention that are described herein provide a method that enables using position tracking systems to measure a position of a sensing-electrode both accurately enough and with reduced complexity of calculations. In some embodiments, position-signals (e.g., electrical currents or impedances) measured with all ACL patches (e.g., six or more) are recorded while one or more sensing-electrodes are being moved through multiple regions in a heart. For any given region, a processor in the position tracking system selects a partial sub-set of least-correlated electrode-patches (also named in the description 'most orthogonal', whereas both terms mean the same). By way of example, three "most orthogonal" of six or more ACL patches are selected. In principle, it is possible that more than three "most orthogonal" ACL patches exist. In practice, however, the benefit of exceeding three patches is small (i.e., not "cost-effective" computationally wise).

The identity of patches making-up a sub-set of least-correlated electrode-patches per given region may be different for impedance and voltage ACL methods. The reason is that in the impedance ACL method, the patches are selected with relation to the sensing-electrodes, whereas in the voltage ACL method the three patches are selected with relation to a fourth patch that serves as a common ground, and whose identity is saved as well. In some embodiments the fourth patch is selected once, so its identity is known and does not need to be restored every time that three newly selected ACL patches have their identity stored.

For a given region of the heart, the processor typically selects a partial subset of the electrode-patches whose position signals are least-correlated with one another (i.e., 'most orthogonal'). The "most orthogonal" ACL patches are selected by examining which pairs of ACL patches provide position-signals that are least-correlated with one another, as the catheter moves about the given region. In other words, when one ACL patch shows a change in signal as the sensing electrode moves, while another patch shows little or no signal change, one of the two ACL patches is selected as one of the nearly orthogonal triplet sub-group for the given region.

The identity of the 'most orthogonal' ACL patches will typically change according to the region being considered and may also change with time. Nevertheless, using such least-correlated ACL patches subgroup (e.g., three) to find the catheter position, instead of, for example, of using data from all (e.g., six) ACL patches, will improve accuracy as the 'most orthogonal' ACL patches provide the required accuracy without degrading the measurement by additional measurement errors that the other, far less significant patches, would still add. Furthermore, using fewer ACL patches reduces the complexity of the real-time calculation. From the computational point of view, by way of example, this largely amounts to processing 3×3 matrices instead of 6×6 matrices, which may yield a significant reduction in the required computational power.

The disclosed technique, thus, has the distinct advantages of (a) improving the position-tracking accuracy, and (b) substantially simplifying real-time calculations. The second advantage will manifest itself, for example, in the reduction of occurrences of disturbing delays between each position measurement step and its subsequent update on a map on a display. The elimination of delays may be especially beneficial for improving the accuracy of a resulting electro-anatomical map of a moving organ such as a heart. Another possible advantage is the reduced requirement on computation hardware in position tracking systems, which may reduce the costs of such medical systems.

System Description

FIG. 1 is a schematic, pictorial illustration of an impedance based Active Current Location (ACL) position sensing system 36, in accordance with an embodiment of the present invention. ACL system 36 is used in determining the position of a mapping-catheter 30, which is fitted at the distal end of a shaft 22, as seen in an inset 25. Mapping-catheter 30 is inserted by physician 56 into an internal body cavity, such as a chamber of a heart 38 of a patient 40. Typically, mapping-catheter 30 is used for diagnostics, such as spatially mapping the heart, and mapping electrical potentials in the heart prior to performing an ablation of heart tissue. Other types of catheters or other intrabody devices may alternatively be used for other purposes, by themselves or in conjunction with other treatment devices.

Mapping-catheter 30 comprises multiple sensing-electrodes 32, seen in an inset 25. Sensing-electrodes 32 are connected by wires through shaft 22 to driver circuitry 44 connected to a processor 46 that is included in a console 24, whereas driver circuitry 44 drives sensing-electrodes 32 as commanded by processor 46. Processor 46 is typically a general-purpose computer, with suitable front end, interface circuits for receiving signals from ACL patches 60P, and appropriate signal processing circuits. For that, driver circuitry 44 is connected by wires through cable 39 to six ACL electrodes attached to the skin of the patient, which are named hereinafter ACL patches 60, 62, 64, 66, 68 and 70, or collectively named hereinafter 'ACL patches 60P'. As seen, ACL patches 60P are placed at the chest and back around heart 38 of patient 40.

Each of six ACL patches 60P receives position signals from each of the one or more sensing-electrodes 32 fitted at mapping-catheter 30, indicative of the position of the one or more sensing-electrodes 32. The six position signals are further processed by processor 46 to derive the positions of each of mapping-electrodes 32 inside heart 38 (namely the ACL method). Driver circuitry 44 drives a display 52, which may show the positions of each of mapping-electrodes 32 inside heart 38.

The method of electrode position sensing using ACL system 36 is implemented in various medical applications, for example, in the CARTO™ system, produced by Biosense Webster Inc. (Irvine, Calif.) and described in detail in U.S. Pat. Nos. 7,756,576, 7,869,865, 7,848,787, and 8,456,182 whose disclosures are all incorporated herein by reference. The number of ACL patches can be larger than six, whereas using six ACL patches is described by way of example.

Processor 46 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Position sensing system 36 may be used with probes similar to mapping-catheter 30 in other body cavities. Typically, system 36 includes other elements, which are not shown in the figures for the sake of simplicity, and which are referred to as necessary in the following description. For example, system 36 may include an ECG monitor, coupled to receive signals from one or more body surface ECG electrodes, so as to provide an ECG synchronization signal to console 24. As another example, system 36 there may comprise one or more additional catheters, such as an ablation catheter and/or additional sensing-catheter, which, as said, are not shown for clarity. Thus, the configuration of FIG. 1 is an example configuration, which is chosen purely for the sake of conceptual clarity. In alternative embodiments, any other suitable configuration can also be used.

Processor 46 comprises typically a general-purpose processor, which is programmed in software to carry out the functions described herein. The software may be downloaded to the processor in electronic form, over a network, for example, or it may, alternatively or additionally, be provided and/or stored on tangible media, such as magnetic, optical, or electronic memory.

Identifying 'Most Orthogonal' Sets of ACL Patches

Figure 2A:
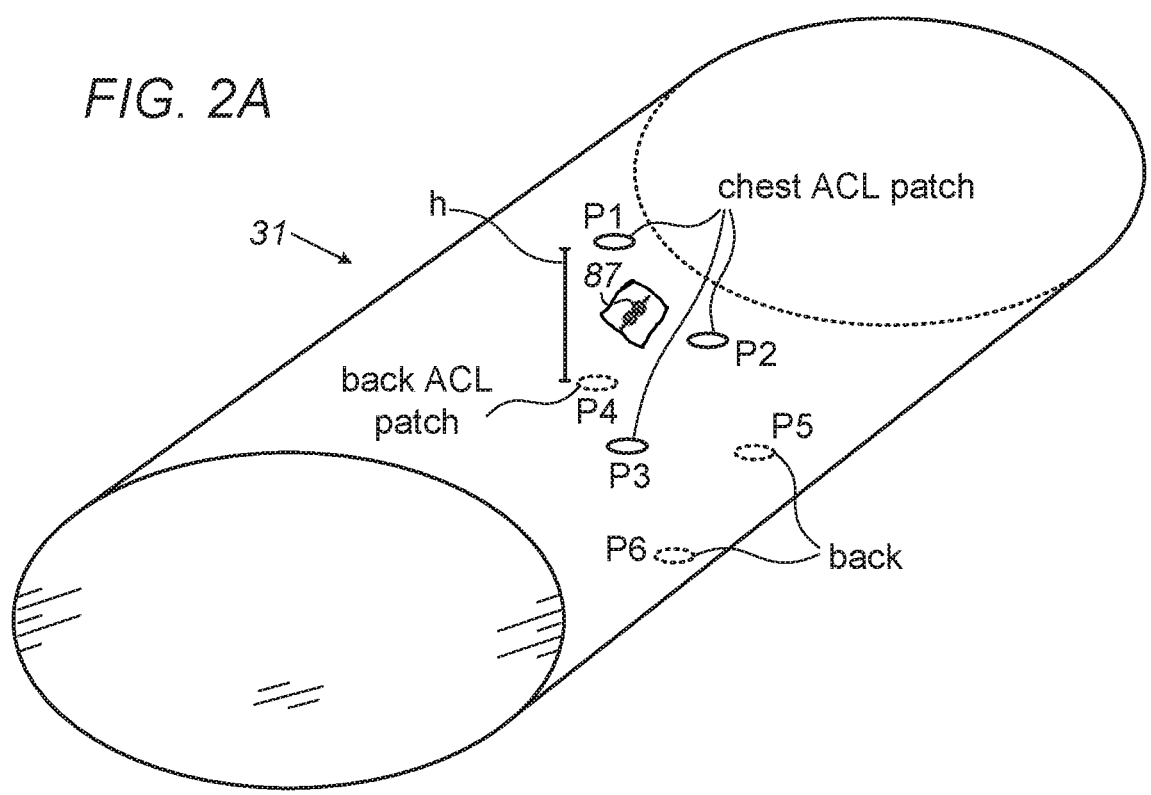
FIGS. 2A and 2B are schematic, pictorial illustrations of a selection process of three least-correlated ACL patches in an impedance ACL method, in accordance with an embodiment of the present invention.
Figure 2B:
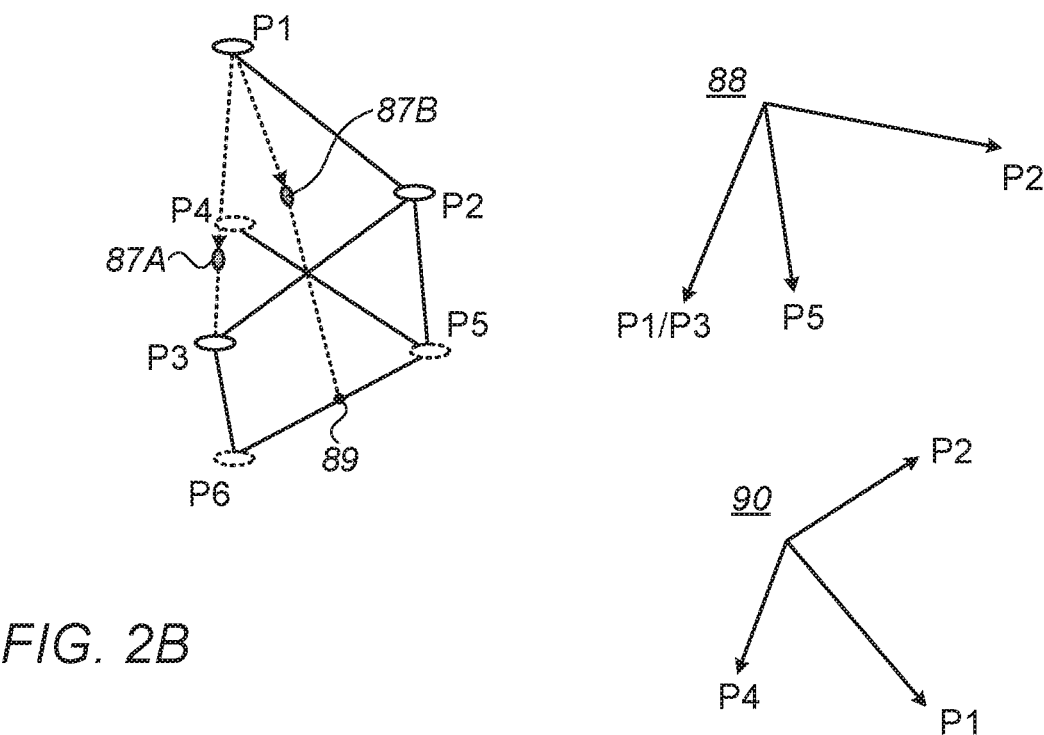

FIGS. 2A and 2B are schematic, pictorial illustration of a selection process of three least-correlated ACL patches in an impedance ACL method, in accordance with an embodiment of the present invention. In FIG. 2A, for clarity, a patient torso 31 is represented by a simplified cylindrical illustration. A position 87 inside torso 31 is measured by six ACL patches, enumerated in FIG. 2A as P1-P6. Patches P1, P2 and P3 are located on the top surface of torso 31 (i.e., 'chest'), while patches P4, P5 and P6 are located on the bottom surface of torso 31 (i.e., 'back'). In such arrangement, the two groups of patches are separated by a typical height denoted in FIG. 2A as 'h'. This separation ensures that any position 34 in torso 31 volume could be reliably spanned by a coordinate space defined by the six ACL patches and an arbitrary origin in space.

Prior to processor 46 selecting three ACL patches, position signals are measured with all ACL patches P1-P6 and recorded as a catheter is being moved about a region 87 in a heart. As explained below, for any given region 87 on an intra-body path that mapping-catheter 30 takes, processor 46 selects three ACL patches, which measure least-correlated change in position signal as the catheter moves. In other words, when one ACL patch shows a changing position signal as catheter 30 moves, while another patch shows little or no change in position signal, one of these ACL patches is selected by processor 46 as one of the three of the subgroup for the given region.

From geometrical point of view, a distance between a patch and a sensing electrode that changes by little or none when the sensing electrode moves, indicates of a suitable patch. Indeed, the little or no change in distance will manifest in little or no change in the position signal measured from that patch, as a change in such signal is largely proportional to a change in the distance.

FIG. 2B exemplifies the selection of three ACL patches for regions 87A and 87B, out of six ACL patches P1-P6. In one exemplified case, region 87A lies on a line that is defined by a catheter 30 moving collinearly with a line connecting ACL patches P1 and P3. Maximal change in position signal is expected on electrodes P1/P3 (which should show anti-correlated signals). As seen, connecting region 87A and positions of patches P2 and P5 by lines would form two largely mutually orthogonal axes relative to a line-axis defined by locations of patches P1 and P3. Thus, a resulting nearly orthogonal coordinate system 88 is defined by patches P1/P3, P2 and P5, which should be sufficient for processor to accurately triangulate region 87A.

In another exemplified case, region 87B lies on a line that is defined by a catheter 30 that moves collinearly with a line connecting ACL patch P1 and point 89 on the line connecting patches P5 and P6. Maximal change in position signal is expected on electrodes P1. As seen, at region 87B, electrode-patches P2 and P4 would form two largely mutually orthogonal line-axes relative to the line-axis connecting P1 and point 89. Thus, a nearly orthogonal coordinate system 90 is defined by P1, P2 and P4, which should be sufficient for processor 46 to accurately triangulate region 87B.

The example pictorial illustration shown in FIGS. 2A and 2B are chosen purely for the sake of conceptual clarity. For example, the number of ACL patches can vary and be larger than six. The selected partial subset least-correlated ACL patches may include more than three patches. Thus, selecting three 'most orthogonal' out of six ACL patches as described in FIGS. 2A and 2B is brought by way of example. As noted above, for a voltage-based tracking system, the three least correlated patches will be selected with relation to a fourth patch that serves as a common ground.

Figure 3:
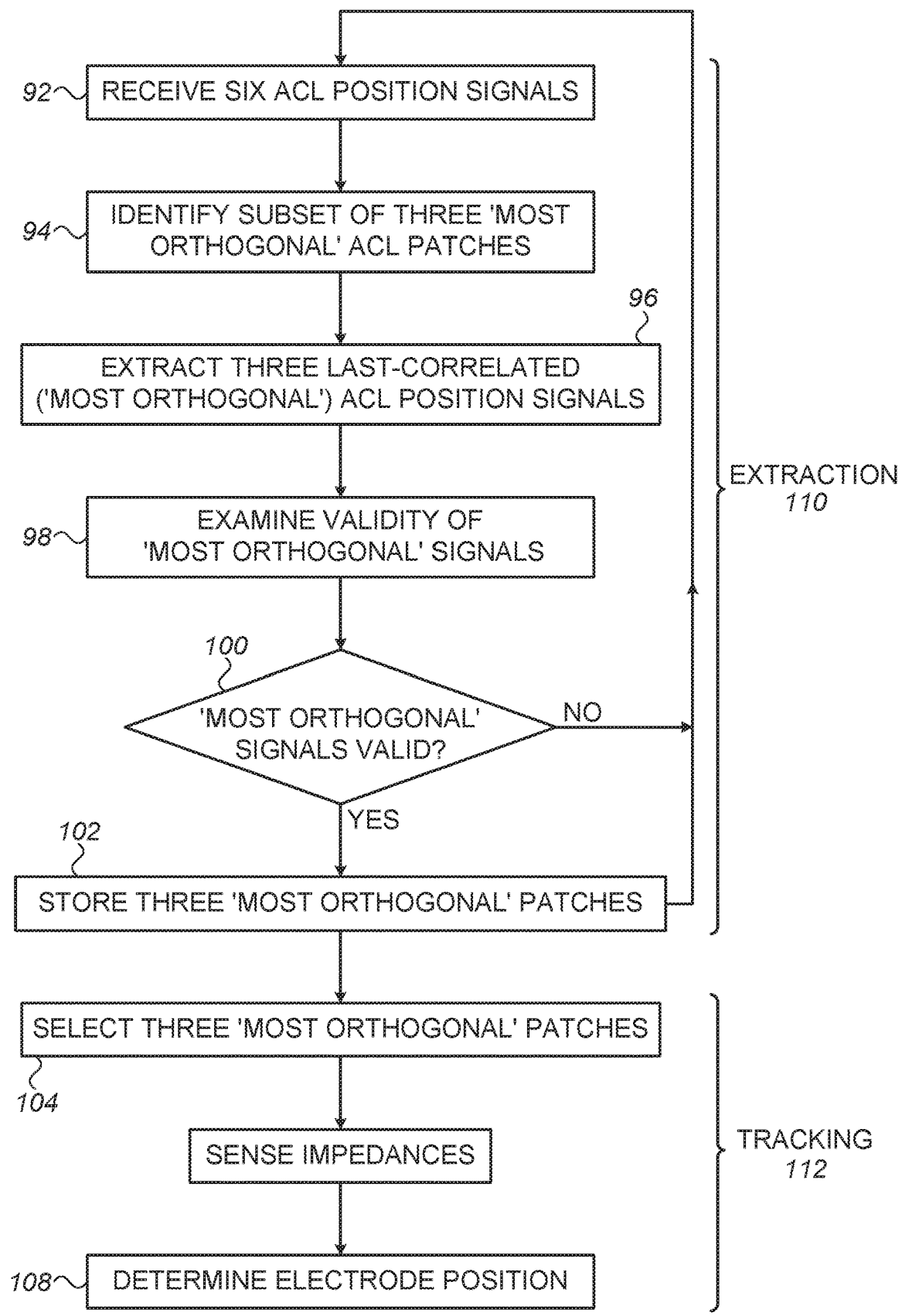
FIG. 3 is a flow chart schematically illustrating a method for obtaining a position of an electrode in the heart, in accordance with an embodiment of the present invention.

FIG. 3 is a flow chart schematically illustrating a method for obtaining a position of an electrode in the heart, in accordance with an embodiment of the present invention. The process begins with an extraction phase 110, after which the system is operated in a tracking phase 112. The two phases may run during at least part of time in parallel, subject to available computation resources.

Extraction phase 110 begins with processor 46 receiving six-position signals from ACL patches 60P, indicative of a position of a sensing-electrode 32 in heart 38, at a receiving step 92.

Next, processor 46 identifies subset of three 'most orthogonal' ACL patches, at an identification step 94. At a following extraction step 96, processor 46 maintains the three least-correlated signals (named collectively the 'orthogonal' signal) of the original six ones. Processor 46 further tests the validity, or quality of the 'most orthogonal' signal against encoded criteria, at an examination step 98. If the examination results in a rejection, processor 46 ignores the 'most orthogonal' signal and the process loops to receive a new six dependent position-signal, at a decision step 100. If the examination results in an acceptance, processor 46 further stores the 'most orthogonal' signal for future use, at a storing step 102. The process than loops back to step 92, to receive another six-position signal, for example from another sensing-electrode, or from a new region of heart 38, until mapping is completed.

In tracking phase 112, processor 46 selects (i.e., retrieves) per each given region the three 'most orthogonal' patches stored in step 82. The system operates sensing-electrode 32 on catheter to inject electrical current and the 'most orthogonal' patches to measure impedances, at a measurement step 104. Based on the measured impedances, processor 46 derives an exact electrode position, at a determining step 108.

The example flow chart shown in FIG. 3 is chosen purely for the sake of conceptual clarity. In alternative embodiments, additional steps may be performed, such as calibration steps and/or adjustment steps. The number of ACL patches can vary and be larger than six. The selected partial subset least-correlated ACL patches may include more than three patches. When voltage-based tracking is used, processor 46 would further store, to begin with, the identity of a fourth patch that was selected to serve as a common ground.

Although the embodiments described herein mainly address improvements in impedance-based position tracking of a cardiac catheter in a heart, the methods and systems described herein can also be used in other applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A position tracking system, comprising:
an electrical interface configured to:
communicate with one or more electrodes that are coupled to a distal end of a probe inserted into a heart of a patient; and
receive, from a plurality of electrode-patches attached to a skin of the patient, during motion of the one or more electrodes about a region of the heart, position signals that are indicative of positions of the one or more electrodes in the heart; and
a processor, configured to:
select, based on the position signals received during motion of the one or more electrodes in the region of the heart, a partial subset of the electrode-patches, the partial subset consisting of three or more most-orthogonal electrode-patches of the plurality of electrode-patches; and
estimate a position of at least one of the electrodes in the heart, based on the position signals received during motion of the one or more electrodes in the region of the heart, from the selected partial subset of the electrode-patches.

2. The system according to claim 1, wherein the processor selects the partial subset of the electrode-patches by sequentially selecting each one electrode-patch from each possible pair of the electrode-patches, such that the one electrode-patch of the pair acts as a reference electrode, while the other electrode-patch measures a changing position signal against a reference signal generated by the reference electrode.

3. The system according to claim 1, wherein the processor is configured to select different partial subsets of the plurality of electrode-patches for different regions in the heart.

4. The system according to claim 1, wherein the electrical interface is further configured to receive the position signals from the one or more electrodes that are coupled to the distal end of the probe.

5. A position tracking method, the method comprising:
communicating with one or more electrodes that are coupled to a distal end of a probe inserted into a heart of a patient;
moving the one or more electrodes about a region of the heart;
receiving, during the step of moving the one or more electrodes, from a plurality of electrode-patches attached to a skin of the patient, position signals that are indicative of positions of the one or more electrodes in the heart;

based on the position signals received during the step of moving the one or more electrodes, selecting a partial subset of the electrode-patches, the partial subset consisting of three or more most-orthogonal electrode-patches of the plurality of electrode-patches; and based on the position signals received from the selected partial subset of the electrode-patches, estimating a position of at least one of the electrodes in the heart.

6. The method according to claim 5, wherein selecting the partial subset comprises sequentially selecting each one electrode-patch from each possible pair of the electrode-patches, such that the one electrode-patch of the pair acts as a reference electrode, while the other electrode-patch measures a changing position signal against a reference signal generated by the reference electrode.

7. The method according to claim 5, further comprising:
moving the one or more electrodes about a different region of the heart;
based on the position signals received during the step of moving the one or more electrodes about the different region of the heart, selecting a different partial subset of the electrode-patches, the different partial subset consisting of threee or more most-orthogonal electrode-patches of the plurality of electrode-patches.

8. The method according to claim 5, and comprising receiving the position signals also from the one or more electrodes that are coupled to the distal end of the probe.

9. A system for tracking a position of a probe within a body of a patient, the system comprising:
a console comprising a processor;
a probe insertable into an internal body cavity of the patient, the probe having one or more sensing-electrodes coupled to a distal end of the probe, the sensing-electrodes driven by driver circuitry;
three or more electrode-patches for attachment to the patient's skin, the electrode-patches configured to receive position signals from each of the one or more sensing-electrodes, the position signals indicative of the position of the one or more sensing-electrodes;
the processor configured to:

(a) record position signals from all of the electrode-patches while the probe is moved about a first region in the body of the patient;
(b) identify three most-orthogonal electrode-patches for the first region based on the recorded position signals;
(c) extract three most-orthogonal position signals for the first region based on the identification;
(d) examine validity of the three most-orthogonal position signals for the first region against an encoded criterion;
(e) if the examination results in a rejection, loop back to step (a);
(f) if the examination results in acceptance, store the three most-orthogonal position signals for the first region; and
(g) while the probe is in the first region, retrieve and use the three most-orthogonal position signals for the first region to track the position of the probe in the first region.

10. The system of claim 9 wherein the processor is further configured to:
(h) record position signals from all of the electrode-patches while the probe is moved about a second region in the body of the patient;
(i) identify three most-orthogonal electrode-patches for the second region based on the recorded position signals;
(j) extract three most-orthogonal position signals for the second region based on the identification;
(k) examine validity of the three most-orthogonal position signals for the second region against an encoded criterion;
(l) if the examination results in a rejection, loop back to step (h);
(m) if the examination results in acceptance, store the three most-orthogonal position signals for the second region; and
(n) while the probe is in the second region, retrieve and use the three most-orthogonal position signals for the second region to track the position of the probe in the second region.

* * * * *